United States Patent
Ries et al.

(10) Patent No.: US 9,220,902 B2
(45) Date of Patent: Dec. 29, 2015

(54) IMPLANTABLE MEDICAL DEVICE CONSTRUCTION

(71) Applicant: Medtronic, Inc., Minneapolis, MN (US)

(72) Inventors: Andrew J Ries, Lino Lakes, MN (US); Terrence J Snyder, Andover, MN (US); Iryna M Levina, Blaine, MN (US); Robert A Munoz, Andover, MN (US); Eric J Wengreen, Sammamish, WA (US); John E Lovins, Oakdale, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 14/179,795

(22) Filed: Feb. 13, 2014

(65) Prior Publication Data
US 2015/0165196 A1    Jun. 18, 2015

Related U.S. Application Data

(60) Provisional application No. 61/916,486, filed on Dec. 16, 2013.

(51) Int. Cl.
| | |
|---|---|
| *A61N 1/00* | (2006.01) |
| *A61N 1/362* | (2006.01) |
| *B23K 26/24* | (2014.01) |
| *H01M 10/42* | (2006.01) |
| *H01M 2/10* | (2006.01) |

(Continued)

(52) U.S. Cl.
CPC .............. *A61N 1/362* (2013.01); *A61N 1/3758* (2013.01); *B23K 26/24* (2013.01); *H01M 2/1022* (2013.01); *H01M 10/425* (2013.01); *A61N 1/378* (2013.01); *A61N 1/3754* (2013.01)

(58) Field of Classification Search
CPC . A61N 1/375; A61N 1/37223; A61N 1/3787; A61N 1/05; A61N 1/08; A61N 1/3752; A61N 1/3754
See application file for complete search history.

(56) References Cited

U.S. PATENT DOCUMENTS

| | | |
|---|---|---|
| 5,573,551 A | 11/1996 | Lin et al. |
| 5,814,091 A | 9/1998 | Dahlberg et al. |

(Continued)

FOREIGN PATENT DOCUMENTS

| | | |
|---|---|---|
| DE | 20 2010 012 154 U1 | 12/2010 |
| DE | 20 2010 012 164 U1 | 12/2010 |

OTHER PUBLICATIONS (PCT/US2014/068480) PCT Notification of Transmittal of the International Search Report and the Written Opinion of the International Searching Authority.

*Primary Examiner* — Robert N Wieland
(74) *Attorney, Agent, or Firm* — Michael C. Soldner

(57) ABSTRACT

An implantable medical device includes two conductive enclosures that are attached together, wherein the first enclosure contains electronics, and the second enclosure contains a power source. The second enclosure, all or a portion of which is located outside the first enclosure, includes an inner layer, an outer layer, and a header plate, all of which are configured to provide redundant sealing for the power source. The inner and outer layers, formed by separate metal sheets nested one within the other, are preferably in direct mechanical and electrical contact. The first sheet, which forms the inner layer, approximately conforms to a profile of the power source, located therein, and the second sheet, which forms the outer layer, conforms to a profile of the first sheet. An insulative housing, which contains connector contacts of the device, is directly secured to the first and second conductive enclosures, for example, by mounting brackets.

14 Claims, 9 Drawing Sheets

(51) Int. Cl.
*A61N 1/375* (2006.01)
*A61N 1/378* (2006.01)

(56) References Cited

U.S. PATENT DOCUMENTS

| | | |
|---|---|---|
| 7,544,220 B2 | 6/2009 | Zhao et al. |
| 7,647,110 B2 | 1/2010 | Hornfeldt et al. |
| 8,359,098 B2 | 1/2013 | Lund et al. |
| 8,433,409 B2 | 4/2013 | Johnson et al. |
| 8,541,131 B2 | 9/2013 | Lund et al. |
| 2003/0040781 A1* | 2/2003 | Larson et al. ............ 607/36 |
| 2005/0228456 A1 | 10/2005 | Hornfeldt et al. |
| 2013/0079600 A1 | 3/2013 | Engmark et al. |

* cited by examiner

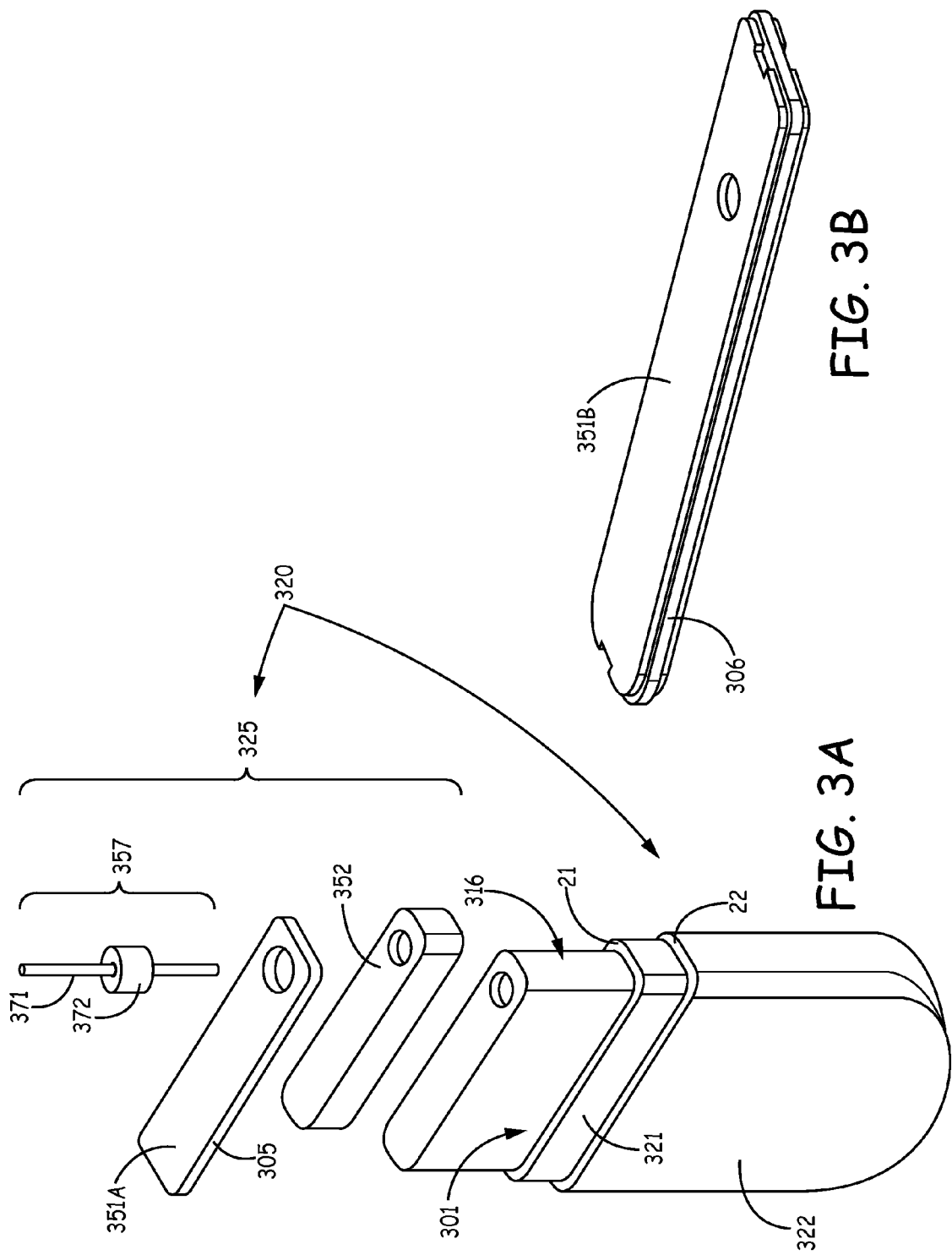

IMPLANTABLE MEDICAL DEVICE CONSTRUCTION

CROSS-REFERENCE TO RELATED APPLICATIONS

This application claims the benefit of U.S. Provisional Application No. 61/916,486, filed on Dec. 16, 2013. The disclosure of the above application is incorporated herein by reference in its entirety.

FIELD OF THE DISCLOSURE

The present disclosure pertains to implantable medical electrical devices, and, more particularly, to constructions thereof.

BACKGROUND

Implantable medical systems that are designed to deliver electrical stimulation, for example, to cardiac muscle or the spinal cord, typically include a pulse generator device to which one or more elongate electrical leads are coupled, for example, like the exemplary system schematically shown in FIG. 1A. FIG. 1A illustrates the system including a device 100, which is implanted subcutaneously in a pectoral region of a patient 12, and a pair of leads 110, which are connected to device 100. Leads 110 are shown extending distally from device 100, and into the venous system of patient 12, so that electrodes thereof are positioned for cardiac sensing and stimulation. A terminal connector assembly of each lead 110 is plugged into a corresponding receptacle of an insulative housing 101 of device 100, for electrical connection to device connector contacts, which are mounted within the receptacles. FIG. 1A further illustrates device 100 including a conductive enclosure 103 to which insulative housing 101 is attached. With reference to FIG. 1B, which is a plan view of device 100 having a portion of enclosure 103 removed, electronics 14 and an associated power source 16, for example, a battery assembly, are contained within conductive enclosure 103, and a feedthrough assembly 115 (FIG. 4), such as is known in the art, electrically couples electronics 14 to the aforementioned connector contacts.

With further reference to FIG. 1A, the comfort of patient 12 may be enhanced if a volume of device 100 is minimized. Yet the operational life of device 100 depends, at least in part, upon the longevity of power source 16, which, if power source 16 is a battery assembly, can directly depend upon the battery cell volume thereof—the larger the volume of the battery cell, the longer the life thereof. Thus there is a need for new implantable medical device constructions that increase packaging efficiency, so that the volume of the power source may be increased without significantly increasing an overall volume of the device.

SUMMARY

The operational life of an implantable medical device, for example, a pulse generator for treating cardiac arrhythmias, may be prolonged by increasing a packaging efficiency thereof, so as to maximize the volume of a power source of the device, without significantly increasing an overall volume of the device, and without compromising reliable construction integrity. According to embodiments and methods disclosed herein, such a device includes a package formed by two conductive enclosures that are attached together, wherein the first conductive enclosure contains electronics of the device, and a second conductive enclosure, all or a portion of which is located outside the first conductive enclosure, contains a power source of the device, for example, a battery assembly, and includes an inner layer, an outer layer, and a header assembly configured to provide redundant sealing for the power source of the device.

The inner and outer layers of the second conductive enclosure are preferably formed by separate metal sheets, which are nested one within the other, and may be in direct mechanical and electrical contact with one another, or, in some cases, electrically isolated from one another. The metal sheets for the second enclosure are preferably formed by a deep drawing method, either together or separately. The first sheet, which forms the inner layer, approximately conforms to a profile of a power source that is located therein, and the second sheet, which forms the outer layer, conforms to a profile of the first sheet. According to some embodiments, the header assembly of the second enclosure includes a header plate having a hermetically sealed feedthrough extending therethrough, wherein the feedthrough electrically couples the power source to the electronics, and wherein the header plate extends over an opening into the second enclosure, which is defined by an edge of the first sheet. The edge of the first sheet is preferably recessed from an edge of the second sheet. The second enclosure further includes at least two welds that extend around an entire perimeter of the header plate, the first of which joins the header plate to the edge of the first sheet and provides a seal for the power source within the second enclosure, and the second of which joins the header plate to the second sheet, in proximity to the edge thereof, and provides a redundant seal for the power source.

In some embodiments, the second enclosure includes another header plate, which also has the aforementioned feedthrough extending therethrough, and a third weld that extends around an entire perimeter of the other header plate to join the other header plate to the edge of the second sheet and to provide another redundant seal for the power source. In some additional embodiments, the first conductive enclosure comprises a metal sheet that contains the electronics, a header plate having a hermetically sealed feedthrough extending therethrough, for electrical coupling with the contained electronics, and a weld extending around an entire perimeter of the header plate of the first conductive enclosure. The sheet of the first enclosure includes an edge that defines an opening into the first enclosure, and the weld of the first enclosure joins the header plate to the edge thereof and provides a seal for the contained electronics.

According to some embodiments, a portion of the first enclosure is inserted within a perimeter of the edge of the second sheet of the second enclosure, when the enclosures are attached together. According to some alternate embodiments, the edge of the second sheet of the second enclosure is inserted within an opening into the first enclosure, such that the edge of a sheet of the first conductive enclosure overlaps the edge of the second sheet of the second enclosure, when the enclosures are attached together. Finally, according to some embodiments and methods, an insulative housing of the device, which contains connector contacts mounted within a receptacle thereof, is secured to the first and second conductive enclosures of the device, for example, by mounting brackets, wherein a first pair of mounting brackets secures a first end of the insulative housing to the first conductive enclosure, and a second pair of mounting brackets secures a second end of the insulative housing to the second conductive enclosure.

BRIEF DESCRIPTION OF THE DRAWINGS

The following drawings are illustrative of particular embodiments of the present disclosure and therefore do not limit the scope of the invention as claimed. The drawings are not to scale (unless so stated) and are intended for use in conjunction with the explanations in the following detailed description. Embodiments will hereinafter be described in conjunction with the appended drawings wherein like numerals/letters denote like elements, and:

FIG. 3A is an exploded perspective view of a conductive enclosure and associated power source of the device, according to some embodiments;

FIG. 3B is a perspective view of a portion of a conductive enclosure, according to some alternate embodiments;

DETAILED DESCRIPTION

The following detailed description is exemplary in nature and is not intended to limit the scope, applicability, or configuration of the invention in any way. Rather, the following description provides practical examples, and those skilled in the art will recognize that some of the examples may have suitable alternatives. Examples of constructions, materials, dimensions and fabrication processes are provided for select elements and all other elements employ that which is known by those skilled in the art.

Figure 1A:
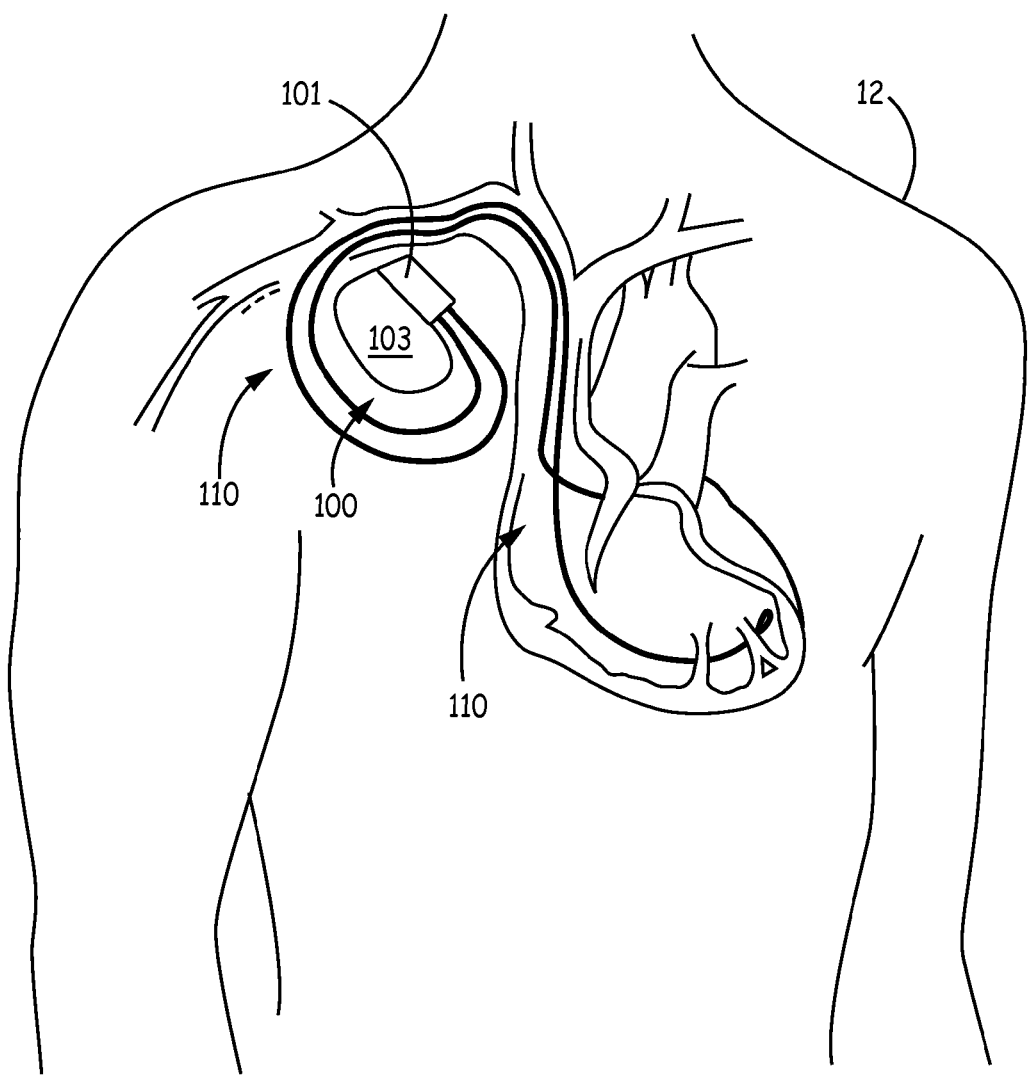
FIG. 1A is a schematic of an exemplary implantable medical electrical system.
Figure 1B:
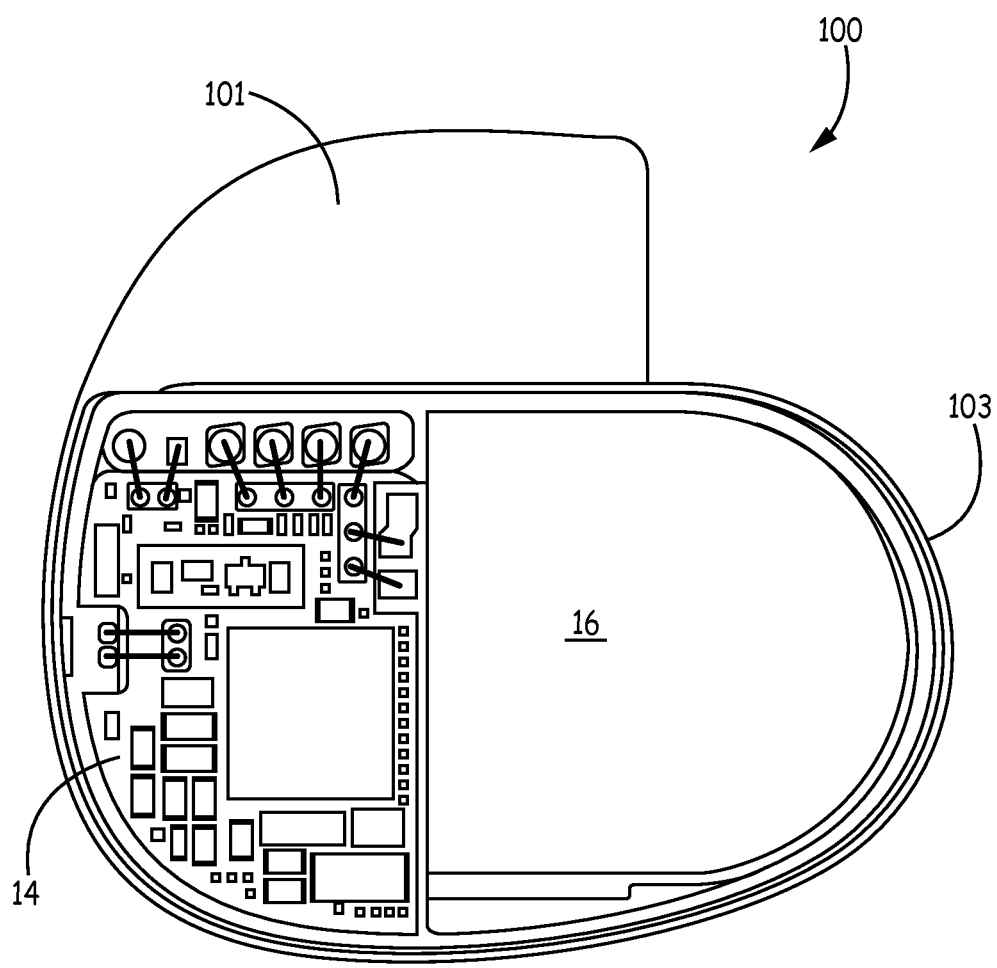
FIG. 1B is a plan view of an exemplary implantable device that may be part of the system shown in FIG. 1A.
Figure 2A:
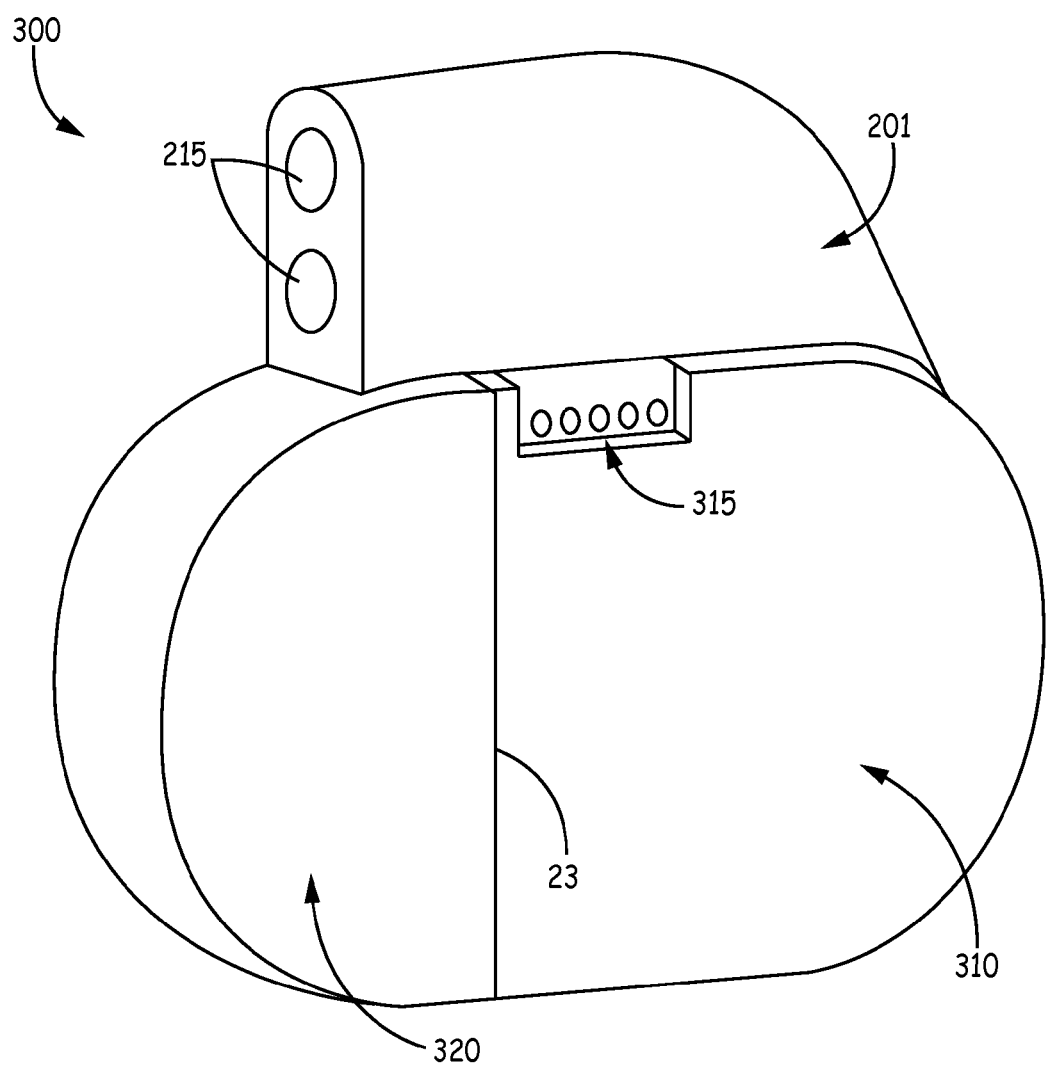
FIG. 2A is a perspective view of an implantable medical device, according to some embodiments of the present disclosure.
Figure 2B:
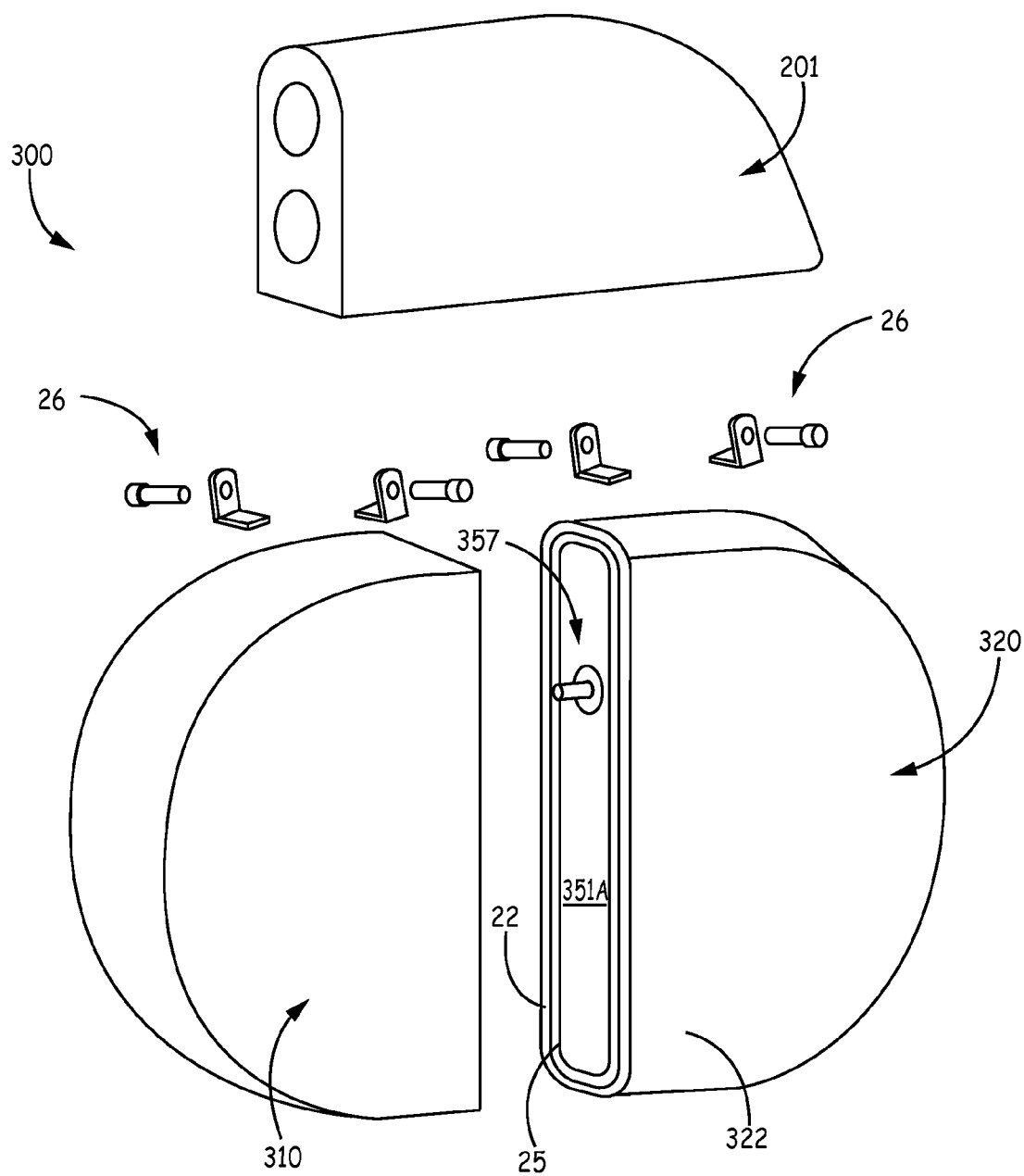
FIG. 2B is an exploded perspective view of the device shown in FIG. 2A, according to some embodiments.

FIG. 2A is a perspective view of an implantable medical device 300, according to some embodiments of the present disclosure. FIG. 2A illustrates device 300 including a first conductive enclosure 310, a second conductive enclosure 320, and an insulative housing 201. First conductive enclosure 310 contains electronics of device 300, for example, electronics 14 shown in FIG. 1B, and second conductive enclosure 320 is attached to first enclosure 310 by a junction 23, for example a welded seam that extends around an entire perimeter of both enclosures 310, 320. FIG. 2A further illustrates insulative housing 201 of device 300 having receptacles 215 formed therein, wherein connector contacts (not shown) are mounted in each receptacle 215 for connecting to a medical electrical lead connector, and each connector contact is coupled to the electronics contained in first conductive enclosure 310 via a hermetically sealed feedthrough assembly 315, which is configured according to constructions and methods known in the art. According to some preferred embodiments, insulative housing 201 is directly secured to both first and second enclosures 310, 320, for example, by mounting brackets 26, which are shown in FIG. 2B.

According to embodiments of the present disclosure, second conductive enclosure 320 is configured to contain a power source, for example, a battery assembly 316 described below, in conjunction with FIG. 3A; second enclosure 320 approximately conforms to a profile of battery assembly 316 to maximize the volume of the battery cell thereof within a given overall volume of device 300. With reference to FIG. 2B, according to some embodiments, second conductive enclosure 320 includes a hermetically sealed feedthrough 357 for electrically coupling battery assembly 316 to electronics 14. FIG. 2B is an exploded perspective view of device 300, according to some embodiments, wherein is shown a header plate 351A is shown having a hermetically sealed feedthrough 357 extending therethrough, both of which may be part of a header assembly 325 of second enclosure 320, which is described below in conjunction with FIG. 3A.

FIG. 3A is an exploded perspective view of second conductive enclosure 320 and the associated power source 316, according to some embodiments. FIG. 3A illustrates second enclosure 320 including a first metal sheet 321, which forms an inner layer of enclosure 320, a second metal sheet 322, which forms an outer layer of enclosure 320, and the aforementioned header assembly 325. According to the illustrated embodiment, first sheet 321 approximately conforms to the profile of battery assembly 315 and includes an edge 21 that defines an opening 301 into enclosure 320; and second sheet 322 conforms to a profile of first sheet 321, preferably being in direct mechanical and electrical contact therewith. The conforming profiles of sheets 321, 322 are seamless, and sheets 321, 322 are preferably formed by a deep drawing method known in the art, either together or separately. Sheets 321, 322 may have a thickness from approximately 0.003 inch to approximately 0.005 inch, and may be formed from titanium, or any suitable alloy thereof, or from any other suitable biocompatible and biostable metal known in the art.

Figure 4:
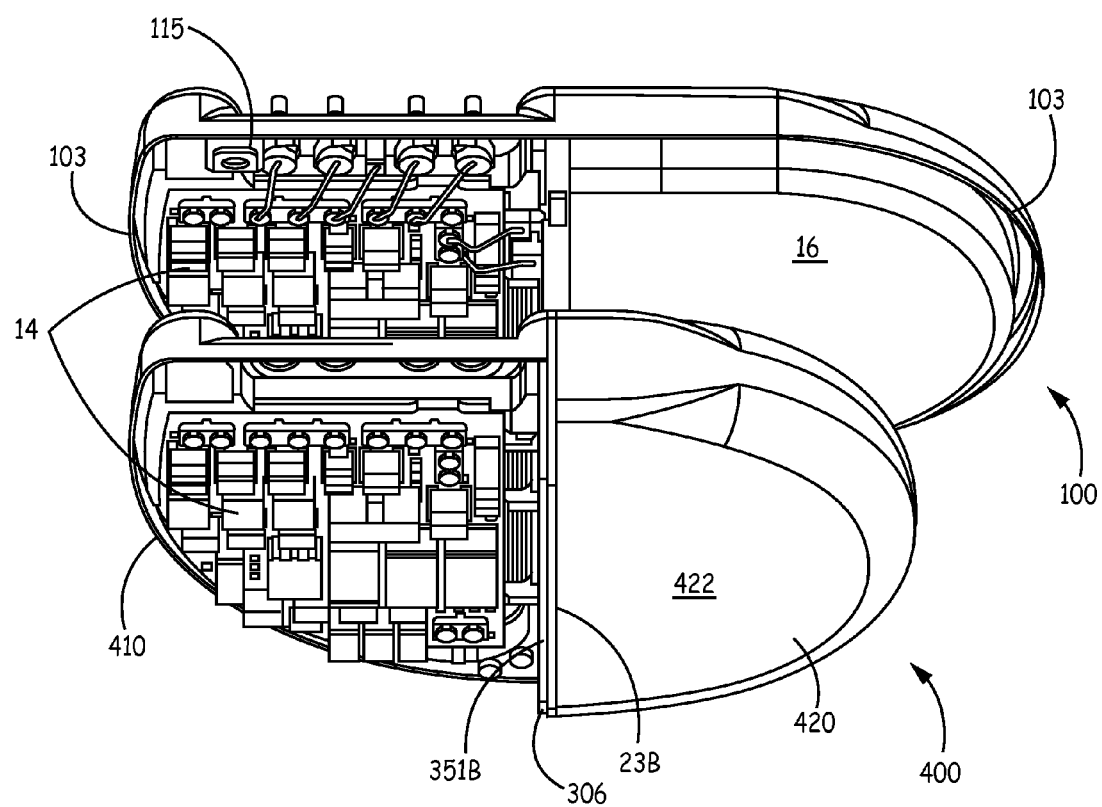
FIG. 4 is a scaled perspective view of a portion of another implantable medical device, according to some embodiments, alongside the exemplary device of FIGS. 1A-B.

The exploded view of FIG. 3A shows battery assembly 315 partially inserted within enclosure 320, through opening 301, and first sheet 321 partially inserted within second sheet 322. With reference back to FIG. 2B, according to some embodiments, header plate 351A extends over opening 301, within edge 22 of second sheet 322 and, being formed of a conductive material, such as titanium, header plate 351A is welded, around an entire perimeter 305 thereof, to both first and second sheets 321, 322, according to some preferred embodiments. FIG. 2B illustrates a weld 25 joining header plate 351A, around an entire perimeter thereof, to second sheet 322 at a location recessed from edge 22 of second sheet 322. Another weld 27, which may be seen in FIG. 5A, extends around an entire perimeter of header plate 351A, joins header plate 351A to first sheet 321, and provides a seal for contained power source 316, such that weld 25, between header plate 351A and second sheet 322, provides a redundant seal for contained power source 316. FIG. 3B illustrates an alternate header plate 351B that includes a flange 306 extending about a perimeter thereof, and which may be substituted for header plate 351A in header assembly 325, according to some embodiments, for example, as illustrated in FIGS. 4 and 5B.

FIG. 3A further illustrates header assembly 325 including a headspace insulator 352, which is located to extend between battery assembly 316 and header plate 351A, when header plate 351A extends over opening 301. Battery assembly 316 may include a battery cell formed by any suitable anode, cathode, and separator, for example, lithium, silver vanadium oxide, and polypropylene film, respectively, which are configured in any suitable manner (e.g., wound, stacked, plate or serpentine), and are contained within a non conductive liner. Headspace insulator 352 may be formed from Ethylene tetrafluoroethylene (ETFE) and configured to protect battery assembly 316 against thermal degradation during welding operations, for example, that form welded seams, for example, junction 23, and/or welds 25, 27, and/or those which are described below. However, according to some alternate embodiments, such an insulator need not be included.

With further reference to FIG. 3A-B, header plate 351A/351B and headspace insulator 352 each have an aperture formed therein to receive an insulator disk 372 of feedthrough 357, through which a feedthrough pin 371 extends. Insulator disk 372, for example, formed any suitable glass (e.g., CABAL-12, or TA-23), is hermetically sealed within the apertures and around feedthrough pin 371, which may be formed from any suitable conductive material (e.g., tantalum, or niobium), according to constructions, configurations and methods that are known in the art. According to the illustrated embodiment, feedthrough pin 371 is configured to electrically couple battery assembly 316 to electronics 14, which are contained in first enclosure 310, when enclosures 310, 320 are attached together.

With reference back to FIGS. 1B and 2A, if we assume that device 100 and device 300 have approximately the same overall volume, and that power source 16 is a battery assembly similar to battery assembly 316, it may be appreciated that the packaging of battery assembly 316 within the profile-conforming second enclosure 320, separate from first enclosure 310, as compared to the packaging of power source 16 in the same enclosure 103 with electronics 14, can allow for an increased volume of the battery cell. For example, a volume of the battery cell of power source may be increased from approximately 3.44 cubic centimeters (cc) to approximately 5.28 cc, when the battery cell is part of battery assembly 316, which is contained within second enclosure 320 of device 300. Given a constant packaged energy density of medium rate cells in this size range, the longevity of the battery cell increases in proportion to the volume increase, so that, in the above example, the increased packaging efficiency of device 300 may give device 300 an increased useful life of up to approximately 50% over device 100. Alternately, an overall volume of device 100 may be reduced without compromising battery cell longevity when the packaging of FIGS. 3A-B is employed. For example, with reference to FIG. 4, an implantable medical device 400 includes a power source/battery assembly packaged in a second enclosure 420, in a similar fashion to the above-described packaging of battery assembly 316 in second enclosure 320, such that a volume thereof, and thus the longevity, is the same as that of power source/battery assembly 16 of device 100. FIG. 4 is a scaled perspective view of device 400 alongside device 100, to illustrate the reduction in overall volume from device 100 to device 400 that is realized when the above-described packaging is employed. FIG. 4 illustrates device 400 including a first enclosure 410, which contains electronics 14, and a second enclosure 420, which includes an outer layer formed by a second metal sheet 422; second sheet 422 conforms to a profile of a first metal sheet (not shown) that forms an inner layer of enclosure 420. Although not seen in FIG. 4, the first metal sheet, which is similar to first sheet 321, approximately conforms to the profile of the corresponding battery assembly, and has an edge that defines an opening into second enclosure 420. FIG. 4 further illustrates header plate 351B extending over the opening into second enclosure 420, and a weld 23B, which is formed between flange 306 of header plate 351B and second sheet 422, and which extends about an entire perimeter of plate 351B, in a fashion similar to that illustrated for second enclosure 320 in FIG. 5B. In either case described above, the dual layer construction of second enclosure 320/420, via incorporation of the first and second metal sheets, facilitates redundant sealing of the corresponding battery assembly within second enclosure 320/420 to maintain a reliable construction integrity for device 300/400.

Figure 5A:
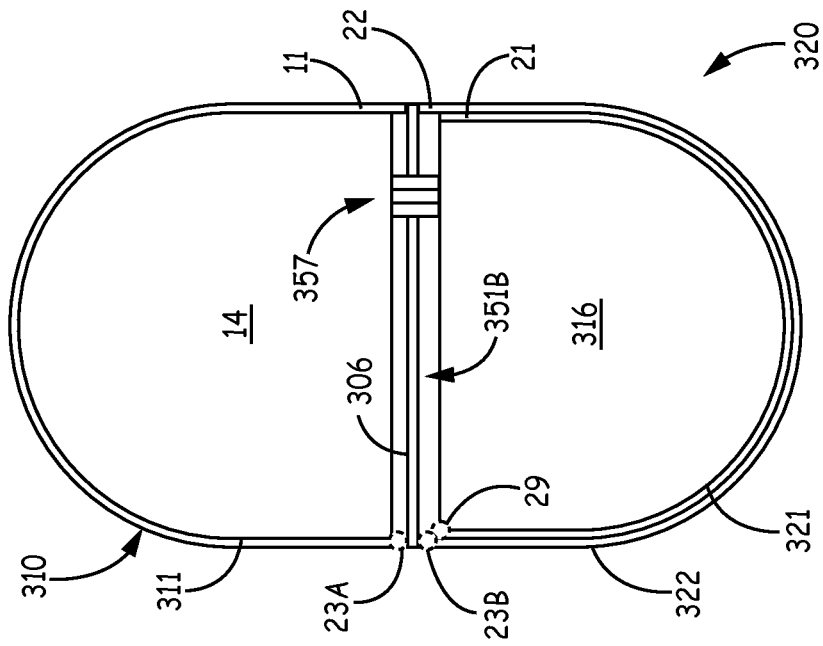
FIGS. 5A-D are plan views, with partial cross-section views, of portions of implantable medical devices, according to some alternate embodiments.
Figure 5B:
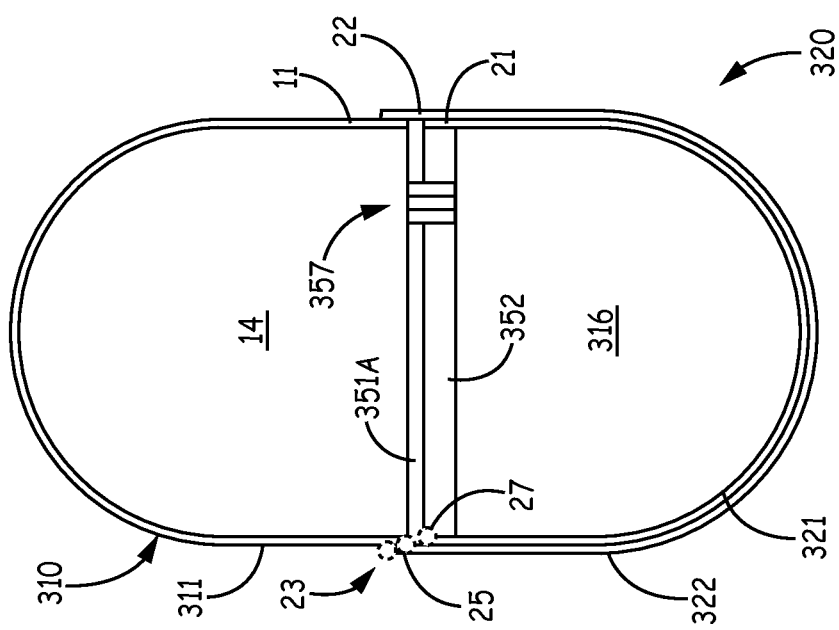

FIG. 5A is a plan view of first and second conductive enclosures 310, 320 of device 300, with a partial cross-section view, according to some embodiments. FIG. 5A illustrates edge 21 of first sheet 321 recessed from edge 22 of second sheet 322, such that edge 22 overlaps a portion of first conductive enclosure 310 in the general location of junction 23 (e.g., the aforementioned weld). FIG. 5A further illustrates the above-described welds 27, 25 formed between header plate 351A and first and second sheets 321, 322, respectively, which provide the redundant sealing of battery assembly 316 within second enclosure 320. FIG. 5B is a plan view, similar to that of FIG. 5A, in which an alternate construction includes header plate 351B, for example, as introduced above, in conjunction with FIGS. 3B and 4. FIG. 5B illustrates flange 306 of header plate 351B sandwiched between edge 22 of second sheet 322 of second enclosure 320 and an edge 11 of a metal sheet 311 of first conductive enclosure 310, such that a weld 23A is formed between sheet 311 and flange 306 of header plate 351B, about an entire perimeter thereof, and alongside the above described weld 23B between flange 306 and second sheet 322 of second enclosure 320. Sheet 311 generally conforms to a profile of electronics 14 contained in first enclosure 310, and edge 11 of sheet 311 defines an opening into first enclosure 310 through which the feedthrough pin of feedthrough 357 extends for coupling to electronics 14. FIG. 5B further illustrates a weld 29 formed between edge 21 of first sheet 321 of second enclosure 320, which is recessed from edge 22 of second sheet 322, and an edge of header plate 351B, which is offset from flange 306, to join header plate 351B to first sheet 321 and to seal battery assembly 316 within second conductive enclosure 320, such that the aforementioned weld 23B provides a redundant seal for battery assembly 316.

Figure 5D:
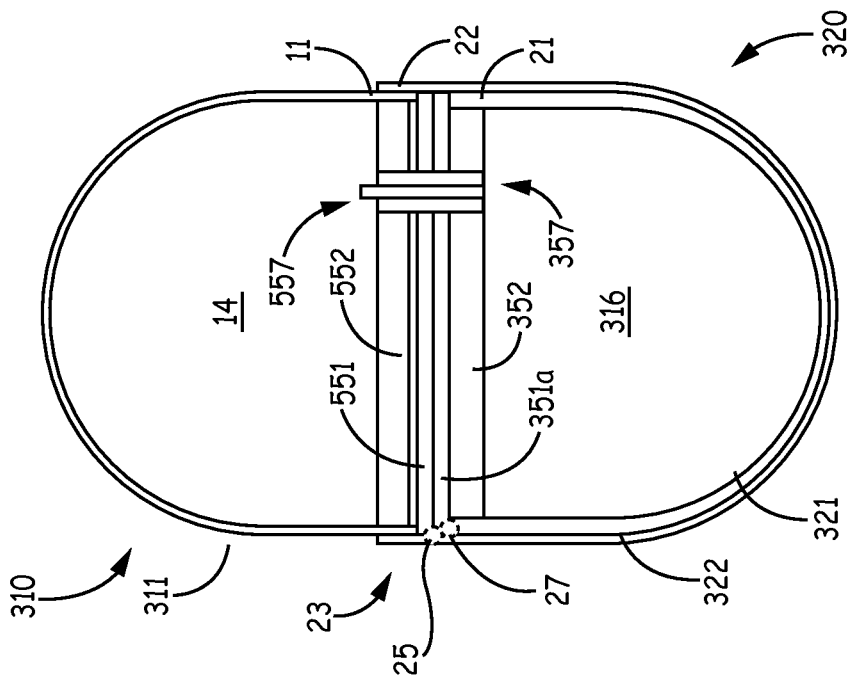
Figure 5C:
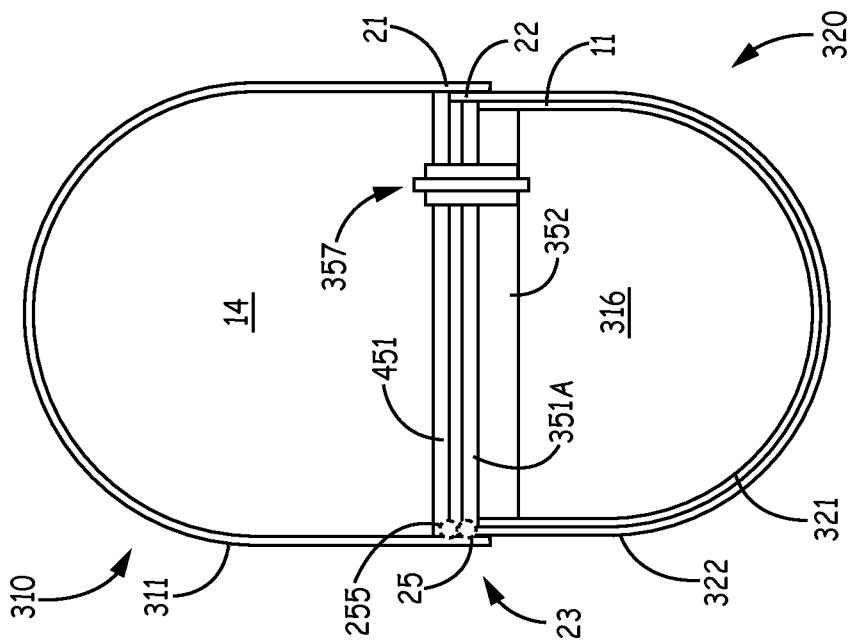

FIG. 5C is a plan view of another construction embodiment, in which the header assembly of second enclosure 320 further includes another header plate 451, which has an aperture through which feedthrough 357 extends. FIGS. 5A and 5C illustrate headspace insulator 352 positioned adjacent edge 21 of first sheet 321, and header plate 351A extending over headspace insulator 352 and over edge 21 of first sheet 321 for the above-described weld 27 (FIG. 5A) between header plate 351A and first sheet 321. According to the embodiment of FIG. 5C, header plate 351A extends over edge 22 of second sheet 322, where another weld 255 is formed around an entire perimeter of header plate 451 to form another redundant seal for battery assembly 316, in addition to that provided by weld 25. FIG. 5C further illustrates edge 11 of sheet 311 of first enclosure 310 overlapping edge 22 of second sheet 322 of second enclosure 320 in the general area of junction 23.

FIG. 5D is a plan view of yet another embodiment, in which first conductive enclosure 310 includes another header assembly, wherein the other header assembly, similar to header assembly 325 (FIG. 3A), includes a headspace insulator 552, a header plate 551, and a feedthrough 557 that extends through an aperture formed through each of headspace insulator 552 and header plate 551. FIG. 5D illustrates headspace insulator 552 received within a perimeter of edge 11 of sheet 311, and header plate 551 extending over headspace insulator 552 and edge 11 of sheet 311. FIG. 5D further illustrates edge 22 of second sheet of second enclosure 320 overlapping edge 11 of sheet 311 of first enclosure 311 in the region of junction 23.

Figure 6:
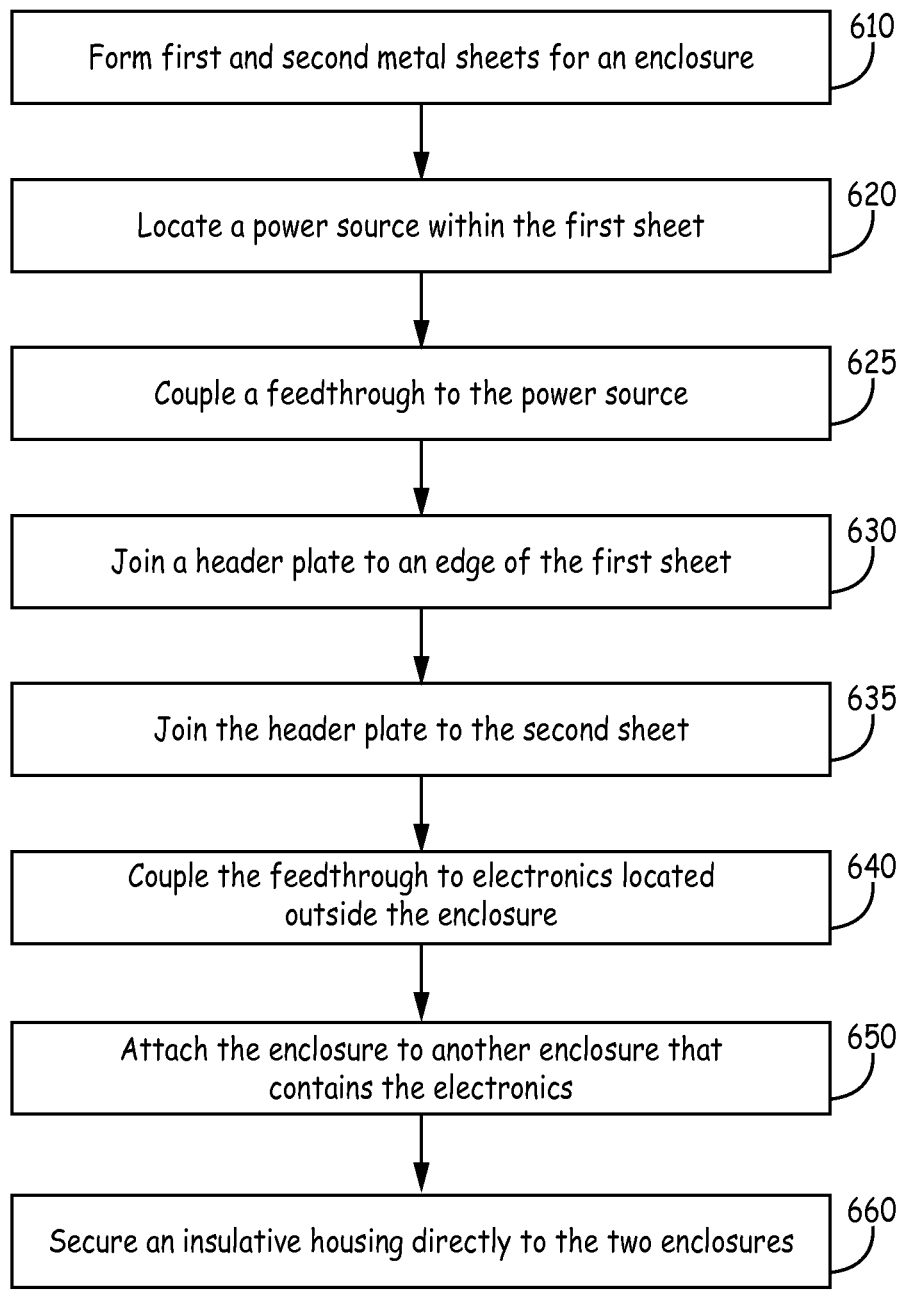
FIG. 6 is a flow chart outlining some methods of the present disclosure.

FIG. 6 is a flow chart outlining some methods of the present disclosure for integrating a power source into an implantable medical device package, for example, battery assembly 316 into any of the above-described packages that include first and second conductive enclosures 310, 320. According to an initial step 610, metal sheets are formed for an enclosure that has an inner layer and an outer layer, for example, second enclosure 320. According to some methods, the metal sheets are placed alongside one another and then deep drawn together, according to methods known in the art, such that a first of the sheets forms the inner layer of the enclosure, and a second of the sheets forms the outer layer of the enclosure. A lubricant may be applied between the sheets to facilitate the drawing process. Alternately, the sheets may be deep drawn separately and then nested together, for example, with the aid of a lubricant. After locating a power source, such as battery assembly 316, within the first sheet/inner layer of the enclosure, per step 620, a feedthrough, for example, of header assembly 325 (FIG. 3A) is coupled to the power source, per step 625, and then a header plate of the header assembly, for example, header plate 351A or 351B, is joined to an edge of the first sheet, per step 630, such that the header plate covers an opening into the enclosure that is defined by the edge of the first sheet. According to some methods, the header plate is joined to the edge of the first sheet by laser seam welding about an entire perimeter of the header plate, after which the second sheet/outer layer of the second enclosure is nested around the first sheet/inner layer and the header plate is joined, in a similar fashion, to the second sheet, per step 635. The weld that joins the header plate to the second sheet is located in proximity to an edge of the second sheet, and, as was described above, provides a redundant seal to that provided by the weld between the header plate and the first sheet/inner layer, for the power source located within the enclosure. Although not included in FIG. 6, according to embodiments like those described above in conjunction with FIG. 5C, another header plate may be joined to second sheet/outer layer of enclosure by a third weld formed between an entire perimeter of the other header plate and the edge of the second sheet/outer layer, after step 635, in order to provide another redundant seal for the power source.

According to step 640, once the enclosure is redundantly sealed, per steps 630 and 635, the feedthrough is coupled to electronics of the device that are located outside the enclosure that contains the power source, for example, electronics 14 that are located within first conductive enclosure 310. Then, per step 650, the two conductive enclosures are attached together, for example, by another laser seam weld at junction 23 shown in FIG. 2A. A portion of the enclosure that contains the electronics may be inserted within a perimeter of the second sheet/outer layer of the enclosure that contains the power source prior to attaching the two enclosures together, for example, resulting in the embodiment of FIG. 5A or that of FIG. 5D. Alternately, a portion of the enclosure that contains the power source is inserted within a perimeter of an edge of a sheet that forms the enclosure for the electronics, prior to attaching the two enclosures together, for example, resulting in the embodiment of FIG. 5B or that of FIG. 5C. Once the two conductive enclosures are attached together, an insulative housing, for example, housing 201, is directly secured to both enclosures, per step 660. According to some methods, a first end of housing 201 is secured to first enclosure 310, and a second end of housing 201 is secured to second enclosure 320, each end by a pair of mounting brackets, for example, mounting brackets 26 shown in FIG. 2B, after which electronics 14 are coupled, via feedthrough assembly 315 (FIG. 2A), to connector contacts, which are mounted within housing receptacles 215.

In the foregoing detailed description, the disclosure makes reference to specific embodiments. However, it may be appreciated that various modifications and changes can be made without departing from the scope of the invention as set forth in the appended claims.

The invention claimed is:

1. An implantable medical device comprising electronics, a power source, connector contacts, a first conductive enclosure containing the electronics, a second conductive enclosure containing the power source, an insulative housing containing the connector contacts, the first conductive enclosure including a feedthrough assembly for coupling the electronics to the connector contacts, all or a portion of the second conductive enclosure being located outside the first conductive enclosure and being attached thereto, and the insulative housing including a receptacle formed therein, the connector contacts being mounted in the receptacle for connecting to a medical electrical lead connector; and wherein the second conductive enclosure comprises:

an inner layer comprising a first metal sheet that approximately conforms to a profile of the power source, the first sheet including an edge defining an opening into the second enclosure;

an outer layer comprising a second metal sheet that conforms to a profile of the first sheet, the second sheet including an edge adjacent to the edge of the first sheet, the edge of the first sheet being recessed from the edge of the second sheet;

a header plate having a hermetically sealed feedthrough extending therethrough, the header plate extending over the opening into the second enclosure, and the feedthrough electrically coupling the power source contained in the second conductive enclosure to the electronics contained in the first conductive enclosure;

a first weld extending around an entire perimeter of the header plate, the first weld joining the header plate to the edge of the first sheet and providing a seal for the contained power source; and a second weld extending around an entire perimeter of the header plate, the second weld joining the header plate to the second sheet, in proximity to the edge thereof, and providing a redundant seal for the contained power source, wherein the first and second metal sheets of the second enclosure are in direct mechanical and electrical contact with one another.

2. The device of claim 1, wherein:

the first conductive enclosure comprises a metal sheet that contains the electronics, the metal sheet of the first conductive enclosure including an edge that defines an opening into the first enclosure; and the edge of the sheet of the first conductive enclosure overlaps the edge of the second sheet of the second conductive enclosure.

3. The device of claim 1, wherein the edge of the second sheet of the second conductive enclosure overlaps a portion of the first conductive enclosure.

4. The device of claim 1, wherein the header plate of the second conductive enclosure includes a flange extending over the edge of the second sheet of the second enclosure; and the second weld joins the flange to the second sheet.

5. The device of claim 4, wherein:

the first conductive enclosure comprises a metal sheet that contains the electronics, the metal sheet of the first conductive enclosure including an edge that defines an opening into the first enclosure; and the edge of the sheet of the first conductive enclosure abuts the flange of the header plate of the first conductive enclosure.

6. The device of claim 1, wherein the second conductive enclosure further comprises:
- another header plate having the hermetically sealed feedthrough extending therethrough, the other header plate extending over the opening into the second enclosure; and
- a third weld extending around an entire perimeter of the other header plate, the third weld joining the other header plate to the edge of the second sheet and providing another redundant seal for the contained power source.

7. The device of claim 1, wherein the first conductive enclosure comprises a metal sheet that contains the electronics, a header plate having a hermetically sealed feedthrough extending therethrough, and a weld extending around an entire perimeter of the header plate of the first conductive enclosure, the sheet of the first enclosure including an edge that defines an opening into the first enclosure, the weld of the first enclosure joining the header plate of the first enclosure to the edge thereof and providing a seal for the contained electronics, and the feedthrough of the first enclosure electrically coupling the electronics to the feedthrough of the second enclosure.

8. The device of claim 1, further comprising a first pair of mounting brackets and a second pair of mounting brackets, the first pair of mounting brackets securing a first end of the insulative housing to the first conductive enclosure, and the second pair of mounting brackets securing a second end of the insulative housing to the second conductive enclosure.

9. A method for integrating a power source into an implantable medical device package, the package comprising a first conductive enclosure and a second conductive enclosure, all or a portion of the second enclosure being located outside the first enclosure, and the first enclosure containing electronics of the device; and the method comprising:
- locating the power source within at least a first metal sheet of the second enclosure, the first sheet forming an inner layer of the second enclosure that approximately conforms to a profile of the power source, the first sheet including an edge that defines the opening into the second enclosure;
- coupling a feedthrough to the power source;
- forming a first weld around an entire perimeter of a header plate to join the header plate to the edge of the first metal sheet and to provide a seal for the located power source;
- locating the first metal sheet within a second metal sheet of the second enclosure such that the edge of the first metal sheet is recessed from an edge of the second metal sheet, the second sheet forming an outer layer of the second enclosure that conforms to a profile of the first sheet;
- forming a second weld around an entire perimeter of the header plate to join the header plate to the second metal sheet, in proximity to the edge thereof, and to provide a redundant seal for the located power source;
- coupling the feedthrough to the electronics of the device; and
- attaching the second enclosure to the first enclosure, after forming the second weld.

10. The method of claim 9, the first conductive enclosure comprises a metal sheet that contains the electronics and includes an edge that defines an opening into the first enclosure; and further comprising inserting the edge of the second sheet of the second enclosure within the opening into the first enclosure, prior to attaching the second enclosure to the first enclosure, such that the edge of the sheet of the first conductive enclosure overlaps the edge of the second sheet of the second enclosure.

11. The method of claim 9, further comprising inserting a portion of the first enclosure within a perimeter of the edge of the second sheet of the second enclosure, prior to attaching the second enclosure to the first enclosure.

12. The method of claim 9, further comprising forming a third weld around an entire perimeter of another header plate, after forming the second weld, to join the other header plate to the edge of the second metal sheet and to provide another redundant seal for the located power source.

13. The method of claim 9, further comprising deep drawing, together, the first and second metal sheets of the second enclosure, prior to locating the power source.

14. The method of claim 9, wherein the package further comprises an insulative housing containing connector contacts and having at least one receptacle formed therein for connecting a medical electrical lead connector to the connector contacts; and the method further comprising:
- securing a first end of the insulative housing directly to the first conductive enclosure;
- securing a second end of the insulative housing directly to the second conductive enclosure, after attaching the second enclosure to the first enclosure; and
- coupling the electronics of the device to the connector contacts via a feedthrough assembly of the first conductive enclosure.

* * * * *